(12) United States Patent
Reina Tosina et al.

(10) Patent No.: US 12,364,416 B2
(45) Date of Patent: Jul. 22, 2025

(54) PORTABLE DEVICE AND METHOD FOR NON-INVASIVE BLOOD GLUCOSE LEVEL ESTIMATION

(71) Applicant: UNIVERSIDAD DE SEVILLA, Seville (ES)

(72) Inventors: Luis Javier Reina Tosina, Seville (ES); Laura Mª Roa Romero, Seville (ES); David Naranjo Hernández, Seville (ES)

(73) Assignee: UNIVERSIDAD DE SEVILLA, Seville (ES)

( * ) Notice: Subject to any disclaimer, the term of this patent is extended or adjusted under 35 U.S.C. 154(b) by 804 days.

(21) Appl. No.: 17/424,734

(22) PCT Filed: Jan. 17, 2020

(86) PCT No.: PCT/ES2020/070027
§ 371 (c)(1),
(2) Date: Jul. 21, 2021

(87) PCT Pub. No.: WO2020/152380
PCT Pub. Date: Jul. 30, 2020

(65) Prior Publication Data
US 2022/0007975 A1    Jan. 13, 2022

(30) Foreign Application Priority Data
Jan. 22, 2019    (ES) .................................. 201930045

(51) Int. Cl.
*A61B 5/145*    (2006.01)
*A61B 5/00*    (2006.01)
(Continued)

(52) U.S. Cl.
CPC ........ *A61B 5/14532* (2013.01); *A61B 5/0002* (2013.01); *A61B 5/1455* (2013.01);
(Continued)

(58) Field of Classification Search
CPC ... A61B 5/0002; A61B 5/1455; A61B 5/6816; A61B 5/6826; A61B 5/7225; A61B 5/7475; A61B 5/0075; A61B 5/14532
See application file for complete search history.

(56) References Cited

U.S. PATENT DOCUMENTS

| | | |
|---|---|---|
| 4,014,321 A | 3/1977 | March |
| 5,448,992 A | 9/1995 | Kupershmidt |

(Continued)

FOREIGN PATENT DOCUMENTS

| | | |
|---|---|---|
| CN | 1194133 A | 9/1998 |
| CN | 101947115 A | 1/2011 |

(Continued)

*Primary Examiner* — Jason M Sims
*Assistant Examiner* — Kyle W. Kretzer
(74) *Attorney, Agent, or Firm* — Hayes Soloway, PC

(57) ABSTRACT

A device which includes a measuring unit with a measuring module for measuring the glucose level, a first computer module for processing data from a first part of the process for measuring the glucose level, a first communications module, a first data storage module and a pushbutton. The device also includes a personal monitoring unit with second and third communication modules, a second computer module for processing data from a second part of the process for measuring the glucose level, an interface module and a second data storage module. Also described is a method for non-invasive blood glucose level estimation.

4 Claims, 6 Drawing Sheets

(51) Int. Cl.
  *A61B 5/1455* (2006.01)
  *A61B 5/024* (2006.01)
  *A61B 5/0531* (2021.01)
  *A61B 5/318* (2021.01)

(52) U.S. Cl.
  CPC .......... *A61B 5/6826* (2013.01); *A61B 5/7207* (2013.01); *A61B 5/7225* (2013.01); *A61B 5/02405* (2013.01); *A61B 5/0531* (2013.01); *A61B 5/14551* (2013.01); *A61B 5/318* (2021.01)

(56) References Cited

U.S. PATENT DOCUMENTS

| | | |
|---|---|---|
| 5,596,450 A | 1/1997 | Hannan et al. |
| 6,015,610 A | 1/2000 | Minor et al. |
| 6,043,492 A | 3/2000 | Lee et al. |
| 6,362,144 B1 | 3/2002 | Berman et al. |
| 6,442,410 B1 | 8/2002 | Steffes |
| 6,704,588 B2 | 3/2004 | Ansari et al. |
| 6,865,408 B1 | 3/2005 | Abbink et al. |
| 6,885,882 B2 | 4/2005 | Cote et al. |
| 7,133,710 B2 | 11/2006 | Acosta et al. |
| 7,299,080 B2 | 11/2007 | Acosta et al. |
| 7,438,855 B2 | 10/2008 | Sota et al. |
| 8,355,767 B2 | 1/2013 | Hunter et al. |
| 8,629,399 B2 | 1/2014 | Thomson et al. |
| 2003/0031597 A1 | 2/2003 | Sota et al. |
| 2003/0174321 A1 | 9/2003 | Samsoondar et al. |
| 2003/0176775 A1 | 9/2003 | Berman |
| 2004/0097796 A1 | 5/2004 | Berman et al. |
| 2004/0225206 A1 | 11/2004 | Kouchnir |
| 2005/0020892 A1 | 1/2005 | Acosta et al. |
| 2005/0043630 A1 | 2/2005 | Buchert |
| 2005/0107676 A1 | 5/2005 | Acosta et al. |
| 2005/0137469 A1 | 6/2005 | Berman et al. |
| 2005/0171413 A1 | 8/2005 | Blair |
| 2005/0192488 A1 | 9/2005 | Bryenton et al. |
| 2007/0027372 A1 | 2/2007 | Hwang et al. |
| 2008/0171925 A1 | 7/2008 | Ku et al. |
| 2009/0004682 A1 | 1/2009 | Kitamura et al. |
| 2009/0116017 A1 | 5/2009 | Xu et al. |
| 2011/0184260 A1 | 7/2011 | Robinson et al. |
| 2015/0164387 A1 | 6/2015 | Varsavsky et al. |
| 2016/0007891 A1 | 1/2016 | Aberg et al. |
| 2016/0058347 A1 | 3/2016 | Reichgott et al. |
| 2016/0100777 A1 | 4/2016 | Bechtel et al. |
| 2016/0157733 A1* | 6/2016 | Gil .................... A61B 5/14551 600/316 |
| 2017/0105663 A1 | 4/2017 | Dhawan |
| 2018/0228433 A1* | 8/2018 | Kim .................... A61B 5/14532 |
| 2020/0155081 A1* | 5/2020 | Seo .................... A61B 5/055 |

FOREIGN PATENT DOCUMENTS

| | | |
|---|---|---|
| CN | 102198004 A | 9/2011 |
| CN | 103344597 A | 10/2013 |
| CN | 103919560 A | 7/2014 |
| CN | 103919561 A | 7/2014 |
| CN | 204318765 U | 5/2015 |
| CN | 104970802 A | 10/2015 |
| CN | 105232055 A | 1/2016 |
| EP | 0534166 A2 | 3/1993 |
| EP | 0807812 A1 | 11/1997 |
| EP | 0869348 A2 | 10/1998 |
| EP | 1137364 | 10/2001 |
| EP | 1346684 A1 | 9/2003 |
| EP | 2086969 A1 | 8/2009 |
| ES | 2086969 T3 | 7/1996 |
| ES | 2093243 T3 | 12/1996 |
| ES | 2101728 T3 | 7/1997 |
| ES | 2102259 T3 | 7/1997 |
| ES | 2133643 T3 | 9/1999 |
| ES | 2206610 T3 | 5/2004 |
| ES | 2313140 T3 | 3/2009 |
| ES | 2314906 T3 | 3/2009 |
| ES | 2445700 T3 | 3/2014 |
| ES | 2582185 T3 | 9/2016 |
| GB | 2482378 A | 2/2012 |
| GB | 2531956 A | 4/2016 |
| JP | H0856565 A | 3/1996 |
| JP | H11188009 A | 7/1999 |
| JP | 2001174405 A | 6/2001 |
| JP | 2004248716 A | 9/2004 |
| JP | 2007175242 A | 7/2007 |
| JP | 2008256398 A | 10/2008 |
| JP | 2010217097 A | 9/2010 |
| KR | 20150122381 A | 11/2015 |
| WO | 9531930 | 11/1995 |
| WO | 0021437 | 4/2000 |
| WO | 0107894 A1 | 2/2001 |
| WO | 0115596 A1 | 3/2001 |
| WO | 0179818 A2 | 10/2001 |
| WO | 02082990 A1 | 10/2002 |
| WO | 03076883 A2 | 9/2003 |
| WO | 2006047273 A2 | 5/2006 |
| WO | 2006079797 A2 | 8/2006 |
| WO | 2008034534 A1 | 3/2008 |
| WO | 2008120936 A1 | 10/2008 |
| WO | 2012048897 A1 | 4/2012 |
| WO | 2013135249 A2 | 9/2013 |
| WO | 2015097190 A2 | 7/2015 |
| WO | 2016086448 A1 | 6/2016 |

* cited by examiner

PORTABLE DEVICE AND METHOD FOR NON-INVASIVE BLOOD GLUCOSE LEVEL ESTIMATION

CROSS-REFERENCE TO RELATED APPLICATIONS AND PRIORITY

This patent application claims priority from PCT Patent Application No. PCT/ES2020/070027 filed Jan. 17, 2020, which claims priority from Spanish Patent Application No. P201930045 filed Jan. 22, 2019. Each of these patent applications are herein incorporated by reference in their entirety.

OBJECT OF THE INVENTION

The object of the invention described herein falls within the area of Information and Communication Technologies (ICT).

More specifically, the object of the invention is located in the context of biomedical engineering and medical technology, as it encompasses the development of portable electronic devices for monitoring physiological variables of people and their health state, in general, and the blood glucose level, in particular.

BACKGROUND OF THE INVENTION

There are 425 million people worldwide who have diabetes mellitus and it is estimated that this number will increase to 629 million in 2045 as a consequence of the population growth and ageing, the increase in urbanisation, the prevalence of obesity, sedentary lifestyles and other unhealthy life habits. One in eleven adults has diabetes and one in seven pregnancies is affected by gestational diabetes. An efficient control of this disease requires blood glucose level tracking. Glucometers, which measure the glucose level starting from blood samples, are the most commonly used devices for measuring glucose due to the precision thereof. This method is painful and annoying, especially in cases wherein a tracking of the glucose level is necessary. In order to prevent this problem, numerous methods for non-invasive blood glucose measurement have been proposed in recent years.

Reverse iontophoresis is based on the flow of a small electrical current through the skin, between an anode and a cathode placed on the surface of the skin. Applying an electrical potential between the anode and the cathode causes the migration of sodium and chloride ions under the skin towards the cathode and anode, respectively. Uncharged molecules, such as glucose, are carried along with the ions following the convective flow. This flow causes the interstitial glucose to be transported through the skin, thus being collected at the cathode, where it is measured by a traditional sensor. The main drawback of this technique is that long exposure times to the electrical potential are required which often tend to cause irritation in the skin. Two examples of patents based on this technique are U.S. Pat. No. 6,885,882 and WO2008/120936.

Impedance spectroscopy is based on the injection of current at multiple frequencies and on the measurement of the voltage produced in the measurement body region. The measurement of glucose is performed indirectly starting from the analysis of the influence thereof on the impedance spectrum. Some examples of patents based on this technique are ES2445700, ES2582185, WO2007/053963, US2005/0192488, US2016/0007891 and US2015/0164387.

Optical coherence tomography is a non-invasive imaging test based on low-coherence light interferometry. The interference pattern obtained contains information on the optical characteristics of the sample and more specifically on the changes in the refractive index which can be used for the glucose level estimation. The main disadvantage of this method is the complexity thereof and the need for expensive and large devices. Furthermore, it is sensitive to the movement of the device, heterogeneity of the tissue, and the interferences with other analytes. The patents US2007/0027372 and US2016/0058347 make use of this method.

Polarimetry is a technique based on the measurement of the optical rotation produced on a polarised light beam when it passes through an optically active substance. Due to the fact that the high scattering coefficient of the skin causes beam depolarisation, most researchers focus their attention on the aqueous humour of the eye. Some limitations of this method are the errors due to eye movement, light exposure safety standards so that no damage occurs, and the discomfort when performing the measurements in the eye. Polarimetry is used in patents ES2313140, U.S. Pat. No. 4,014,321, EP0534166, U.S. Pat. Nos. 6,704,588 and 6,442,410.

Infrared thermal spectroscopy measures the thermal radiation emitted by the human body as a result of changes in glucose concentration. This method has many error sources, such as the movement of the measuring device, the ambient temperature, and the variation in the body and tissue temperatures. US2005/0043630 is an example of a patent based on this method.

Raman spectroscopy is based on the use of a laser beam which induces the rotation and oscillation of the molecules in a solution. The consequent emission of the scattered light is influenced by this vibration of the molecules, which depends on the concentration of the solutes in the solution. Its main disadvantage is that the biological tissue can be damaged due to the powerful laser of the Raman system. This technique is used in ES2093243, ES2206610, ES2314906, U.S. Pat. Nos. 5,448,992, 8,355,767 and US2016/0100777.

Photoacoustic spectroscopy is based on the use of a laser beam to excite a fluid and consequently generate an acoustic response. The photoacoustic signal depends on the specific heat of the tissue, which in turn depends on glucose concentration. The main limitation of this technique is its sensitivity to chemical (other biological compounds) and physical (changes in temperature and pressure) interferences. EP1346684 makes use of this method.

Infrared spectroscopy is based on the absorption of infrared radiation by vibrating molecules. A molecule will absorb energy from a light beam if its vibration frequency matches the light wavelength. This way, glucose concentration can be estimated according to the variation in the intensity of the light crossing through a tissue. As fundamental advantages, it can be highlighted that it is a completely non-invasive technology, the assembly of the systems is simple and the cost is relatively low. Near-infrared (NIR) spectroscopy ranges from 700 nm to 2500 nm and mid-infrared (MIR) spectroscopy ranges from 2500 nm to 10 μm. Given that the present invention is based on the infrared spectroscopy technique, a review of the state of the art on the application of this technique for the estimation of glucose concentration and other analytes is performed below.

Many documents including the use of the infrared spectroscopy technique do not delve into the way in which this technique is implemented, such as CN204318765, and are discarded from the review of the state of the art for this reason.

Patent CN104970802 uses near-infrared spectroscopy in the spectrum range between 1500 nm to 3000 nm, but does not indicate how to obtain the glucose values. The device is integrated into a wristwatch which includes a microprocessor and a Bluetooth transmission module. Furthermore, it includes a gravity sensor for the estimation of steps while walking and a skin temperature sensor.

Patent CN105232055 uses a 1610 nm infrared light source on the earlobe. The device is based on an optical spectroscopy measurement with two trajectories: one for a light beam of which serves as a reference, and another trajectory affected by the reflection on the body measuring area.

In document US2009/004682 a procedure for the estimation of glucose in liquid blood samples is described. They use a method based on the absorption spectrum of infrared light in the wavelength range of 9615 to 9804 nm. For glucose estimation, it uses the integration of the absorption intensity, and the integration of the second derivative of the absorption intensity, although it does not mention how to obtain the absorption spectrum. Patent ES2101728 also uses the second derivative of the absorption intensity, although in the range comprised between 1100 and 1900 nm. This document shows a procedure for the estimation of the absorption spectrum.

In US2008/171925 multiple wavelengths obtained from different sources are used simultaneously, measuring the lag between the incident signal and the reflected signal in order to provide a glucose level estimation. Patent ES2133643 also uses two wavelengths for glucose estimation. The device of patent US2017/105663 performs two spectroscopy measurements in the near-infrared region and fits the data using a convolution function and a Monte Carlo simulation.

The apparatus described in EP0869348 irradiates the measuring area in three wavelengths: a first wavelength related to the absorption peak of the OH group of the glucose molecule (typically 1550 nm to 1650 nm), a second wavelength related to an absorption peak of the NH group (typically 1480 nm to 1550 nm) and a third wavelength related to the absorption peak of the CH group (typically 1650 nm to 1880 nm). It estimates the glucose level starting from the radiation received by means of a multivariate analysis.

According to the procedure shown in EP0807812, a low coherence light beam is irradiated to the eyeball. The beam which is reflected from different depths of the eyeball interferes with another reference light beam reflected from a mirror capable of moving. The method used enables the light coming from the interface between the cornea and the anterior aqueous chamber (aqueous humour) to be separated from the light coming from the interface between the anterior aqueous chamber and the crystalline lens. The optical absorbance of the aqueous humour is calculated from the captured intensities of the two light beams. The process is repeated at different wavelengths in order to obtain the glucose concentration in the aqueous humour.

Patents US2005/0107676 and WO2006/047273 use a broadband infrared light source and different optical filters in order to estimate the absorption spectrum of the infrared light between 1100 and 1900 nm. In order to avoid the influence of the temperature, they include an active temperature control system in the sensor area. Patents US2005/020892 and U.S. Pat. No. 7,299,080 have similar features, but in the range comprised between 1150 to 1850 nm. Furthermore, they use different optical fibers for the access to different detection areas. The use of multiple probes minimises the interference in the sample spectrum due to placement errors.

CN102198004 uses a halogen bulb as an infrared source and a digital signal processor (DSP) for glucose estimation. Such light source emits a range of wavelengths from 600 to 2500 nm, covering the absorption wavelengths bands of glucose and water. It uses the spectrum and a neural network in order to estimate the glucose level.

Patents GB2531956 and WO2015/097190 describe an apparatus for characterising an analyte, which can be glucose, in a superficial layer of the skin. A reflector implanted beneath the superficial layer of the skin receives incident radiation which has passed through the body measuring area and reflects it through it to a sensor located outside the body. It also uses the analysis method of Raman spectroscopy. Furthermore, in order to promote hair growth in the measuring area, the possibility of applying growth factors is indicated.

Invention CN103344597 describes a method for estimating the concentration of sugar and salt in lotus roots. It uses the mid-infrared spectroscopy technique and a model which is calibrated by the least squares method starting from measurements performed on a set of samples with concentrations of 5%, 10%, 15%, 20% of salt and sugar. Patent WO2012/048897 shows a method for classifying sugar beet seeds by means of the absorption spectrum of the samples in the infrared region.

Patent ES2102259 describes a procedure for the analytical determination of glucose concentration in a biological matrix, based on the calculation of the propagation time of light within the biological matrix under study. The method described in US2011/0184260 makes two light sources with different polarisation strike the sample, estimating the glucose from the comparison of the light captured in each polarisation. In contrast, ES2086969 characterises the concentration of glucose level in a biological matrix starting from the light received in two detectors located at different distances with respect to the emitter.

Patent GB2482378 describes an optical device and a method for the non-invasive determination of an analyte concentration in a tissue sample. The device has two optical interfaces whereon the incident light is reflected, the second one being located on the sample. The interfaces are arranged in order to generate an interference pattern as a consequence of the phase difference between the light reflected from the first interface and the light reflected from the second interface. U.S. Pat. No. 6,043,492 makes use of two Fabry-Perot interferometers in order to obtain the absorption spectrum of glucose in the near-infrared region.

The method described in U.S. Pat. No. 8,629,399 enables the evolution of a biological process such as fermentation to be analysed. According to this procedure, the initial absorption spectrum in the mid-infrared region is combined with a reference pattern, which enables the expected spectrum to be predicted when the biological process has concluded. The evolution of the process is analysed by comparing the current spectrum with the expected one.

WO2001/007894 protects a procedure for determining the concentration of an analyte (albumin, cholesterol, glucose, total protein, triglycerides and urea) in a biological fluid comprising the following steps: drying a sample of the fluid on a glass plate in order to produce a film on the plate; directing an infrared beam through the plate and film at an infrared wavelength between 2500 to 5000 nm; and analysing the spectrum thus acquired in order to determine the concentration of the analyte in the film.

Within the analysis by means of infrared spectroscopy, absorption spectroscopy is an analytical technique used to determine the concentration of one or more substances in a sample. Absorption spectroscopy is performed using a device called a spectrophotometer, which in the most basic form thereof is formed by a light source, a sample holder, and a detector. Documents WO2003076883 and U.S. Pat. No. 7,133,710 are based on spectrophotometers which measure different wavelengths in the range from 1180 to 2320 nm. The light produced from the source (incident light) passes through the sample to a detector which measures the amount of light transmitted. For a non-dispersive sample, the absorbance of the sample is proportional to the logarithm of the amount of incident light illuminating a sample divided by the amount of light transmitted through the sample. The incident light is obtained by measuring the amount of light which reaches the detector without the sample. However, it is common that for the light to be transmitted through the sample, the intensity of the incident light must be significantly greater than the amount of light required to saturate the detector.

One method to compensate detector saturation is to use a smaller integration time (time the detector is exposed to light before the measurement) for the reference measurement. However, the use of different integration times for the measurements of the sample and the reference can lead to an error in analyte determinations.

Another method to compensate the saturation of the detector is to attenuate the reference beam with a photometric filter, which enables the intensity of the incident light reaching the detector to be reduced. Patent WO2001/015596 describes an artificial filter made of polytetrafluoroethylene (PTFE) and glass fibre which mimics the absorbance spectrum of a part of the body and includes the spectral components of blood. Other similar patents are U.S. Pat. Nos. 6,015,610 and 5,596,450. However, any variation in the filter as a result of temperature fluctuations can affect the precision in the estimations. Patent US2003/0174321 describes an artificial filter for wavelengths comprised between 600 nm and 1650 nm which is robust to variations in temperature.

Another commonly used method is attenuated total reflection (ATR) infrared spectroscopy. In this method, a light beam is made to strike a crystal. The size and shape of the crystal favour a series of internal reflections before the beam can exit the crystal with the information. The upper surface of the crystal is located on the surface of the sample, which can be the skin. When the infrared beam strikes the crystal upper surface at an angle which exceeds a critical angle, the beam is completely reflected inside the crystal. Each reflection against the upper surface provides a little more information about the sample composition.

The reflected beam includes an evanescent wave which penetrates a short distance into the sample over a wide range of wavelengths. In those regions of the infrared spectrum wherein the sample absorbs radiation, a part of the light does not return back to the crystal. The amount of light absorbed provides the information necessary for the quantification of glucose level.

The patents WO2001/079818, WO2000/021437, EP1137364, US2005/0137469, US2004/225206, US2003/176775, US2005/0171413 and U.S. Pat. No. 6,362,144 are based on the ATR method. In these documents the determination of glucose level is performed starting from the comparative analysis in two specific regions of the infrared spectrum, one of them used as a reference with a wavelength in the range between 8250 and 8750 nm, and the other used as a measurement with a wavelength between 9500 and 10000 nm. JP2001174405 is an invention similar to the previous ones, but it uses a single wavelength generated by a laser and a total reflecting prism as a crystal. Another example is JPH11188009, wherein an ATR prism or an optical fiber is used. WO2006/079797 describes an apparatus for measuring an analyte such as glucose by means of an electrically heated ribbon as an infrared light source, an ATR waveguide, waveguide collimators and light detectors. The collimator and the detector are positioned with respect to the waveguide at an adjustable angle. The value of glucose is obtained by applying a predictive algorithm to measurements taken at different time intervals. The effect of temperature is compensated for with the measurement of a temperature sensor and pressure is controlled by a pressure sensor. Patent WO2016/086448 also includes as an innovative element a pressure sensor in order to normalise the glucose estimations.

The document JP2010217097 describes a spectrometer which includes a light source in the mid-infrared region, an ATR unit, and a set of optical bandpass filters in order to detect the different wavelengths. Each of the filters is activated by means of the rotation of a prism actuated by a motor.

Patents CN103919560 and CN103919561 are also based on the ATR technique, but in this case the reflection element is the end of an optical fiber, which is implanted underneath the skin. The sensitivity of the measurement is reinforced by metal nanoparticles located at the end of the optical fiber. Other documents based on ATR are JPH0856565, which uses different wavelengths comprised between 8333 and 11111 nm in order to estimate the degree of fermentation in a fluid; US2003/031597 and U.S. Pat. No. 7,438,855B2, which use an ATR prism and a customised calibration curve in order to estimate glucose concentration; or US2004/0097796.

CN101947115 describes an implantable system for the measurement of glucose concentration in human blood based on ATR on optical fibre. In this case the light is divided into two different optical paths: in one path the light is coupled to the optical fiber by means of an ATR sensor, in the other path the light received is used directly as a reference signal.

Patent WO2002/082990 uses the infrared spectroscopy technique based on the Fourier transform. Rather than projecting a monochromatic light beam onto the sample, this technique generates a light beam which contains multiple wavelengths at once and measures the amount absorbed by the sample. The process is repeated numerous times, modifying the beam in order to contain different combinations of wavelengths. Finally, a computer infers the absorption at each wavelength starting from all the measurements. Other documents which use the infrared spectroscopy technique by means of the Fourier transform are JP2008/256398, which incorporates a procedure for the elimination of noise generated by water; KR2015/0122381, applied to the estimation of galactose and anhydrous galactose in liquid media; U.S. Pat. No. 6,865,408, which integrates a diffuse reflectance accessory which creates an interferogram, from which a computer system estimates glucose level; WO2013/135249, which uses as a basis a commercial infrared spectrometer based on the Fourier transform (Shimadzu IRPrestige—21/8400S, Japan) and an ATR crystal prism mounted on a PIKE Technologies accessory (ATR-8200 HA), or CN1194133, wherein another commercial spectrometer (Nicolet Magna-IR 750 Series II) is used.

DESCRIPTION OF THE INVENTION

The present invention refers to a device and the method used by such device for non-invasive blood glucose level estimation. The device is preferably formed by two devices: the measuring unit and the personal monitoring unit, communicating with each other wirelessly.

The measuring unit is a portable device which is placed on the skin of an human body area irrigated by a vascular bed, and which emits light at two different wavelengths, one of them corresponding to a maximum absorbance in the absorption spectrum in the glucose molecule within the near-infrared range. The measuring unit also captures the light which crosses through the measuring area, and the personal monitoring unit estimates blood glucose level based on this information, showing the result of the estimation to the user.

With regard to the common devices for measuring the glucose level, glucometers, the main advantage is a innocuous and painless use which prevents any type of discomfort or annoyance to the user. Furthermore, the measurements can be repeated as many times as desired. Another advantage of the proposed device is its low cost, since it uses off-the-shelf electronic components and does not require reactive strips which would increase the ongoing cost of the device. Regarding commercial clinical systems for the automatic/semi-automatic monitoring of glucose in interstitial fluid, the main advantages thereof are also its low cost (it does not need supplements which increase the ongoing cost), safety (it does not require the insertion of elements under the skin that can cause irritations, in addition to the danger of infections that this implies) and the precision thereof, since it analyses the glucose component in blood itself and not that of the interstitial fluid, which can induce errors.

Furthermore, the device has other innovative features and technical advantages:

The measurement principle is based on photoelectric effects, such that the measurements are innocuous and can be repeated as many times as desired without discomfort to the user.

It is a portable system capable of communicating with the outside by means of two-way wireless communications, for the integration of the measurements in an e-Health system in the upstream direction, and the remote configuration and customisation of the device in the downstream direction.

The device object of the invention is based on the technique of infrared spectroscopy. Compared to other proposals based on this technique, the device and method described in the present invention have a series of novelties and innovations: 1) An absolute normalisation consisting of a comparative analysis with respect to a second wavelength unaffected by the presence of glucose molecules. 2) Access to the arterial component of the blood, identifying the pulsating components in the signals captured. 3) A relative normalisation against fluctuations in the light level, movements, and other conditioning factors, consisting of a comparative analysis with respect to the continuous levels in the signals captured. 4) Customisation of the glucose estimation model depending on the particular characteristics of the person and the context wherein the measurement is performed. The novelties of the object of the invention are represented in the set of claims accompanying this description.

DESCRIPTION OF THE DRAWINGS

As a complement to the description provided herein, and for the purpose of helping to make the features of the invention more readily understandable, in accordance with a preferred practical exemplary embodiment thereof, such description is accompanied by a set of drawings which, by way of illustration and not limitation, represent the following.

PREFERRED EMBODIMENT OF THE INVENTION

Figure 1:
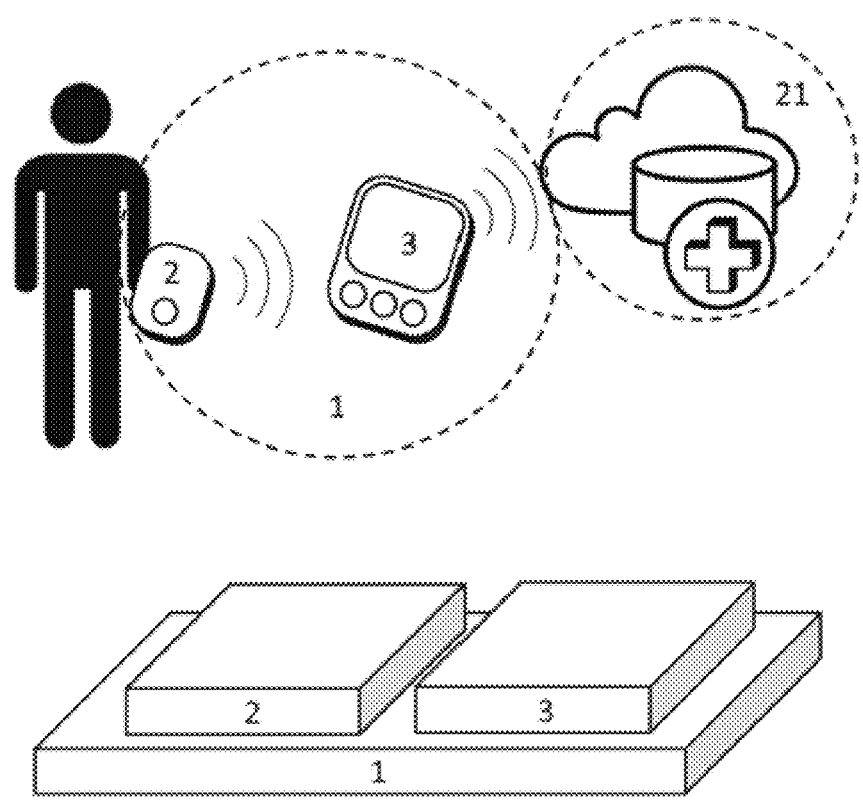
FIG. 1 shows a diagram of the basic architecture of the device object of the patent and the devices which make it up.

In a possible embodiment of a first aspect of the invention proposed here shown in FIG. 1 it has a device (1) for non-invasive blood glucose level estimation, which in a preferred embodiment comprises a device formed by two units: a measuring unit (2) and a personal monitoring unit (3). The device (1) is capable of communicating wirelessly and bidirectionally with an external service provider (21).

Figure 2:
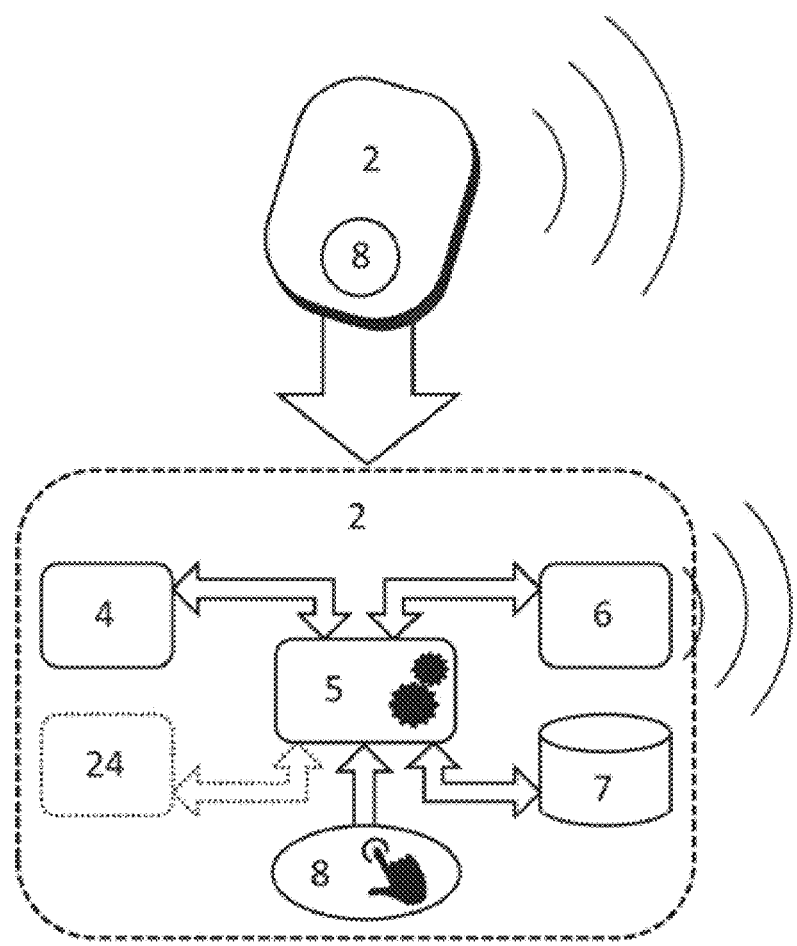
FIG. 2 shows a diagram of the basic architecture of the measuring unit.
Figure 3:
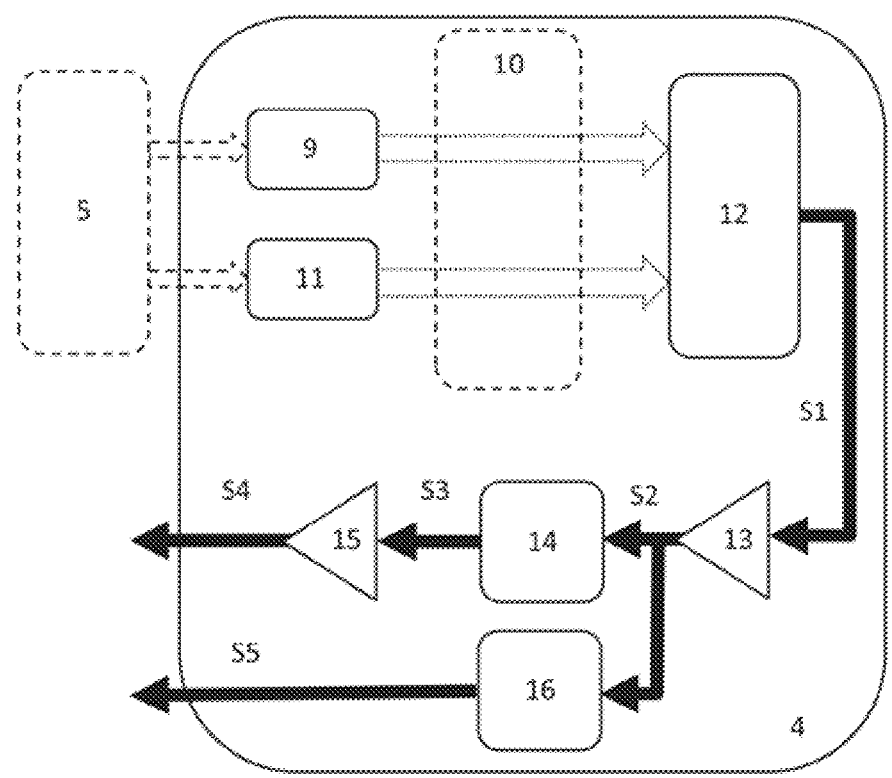
FIG. 3 shows a diagram of the basic architecture of the measuring module.

The measuring unit (2) is a portable device which is placed on the skin of a human area body irrigated by a vascular bed, and which emits light at two different wavelengths, one of them corresponding to a maximum absorbance in the absorption spectrum in the glucose molecule within the near-infrared range. The measuring unit (2) captures the light which crosses through the measuring area, and in conjunction with the personal monitoring unit (3), performs a blood glucose level estimation by means of a computational model based on the following conditions: 1) isolating the influence of the glucose from the relationship existing in the amount of light received at each of the wavelengths; 2) normalising the estimation with respect to the influence of the ambient light and with respect to stationary properties of the measurement such as the level of light emitted, the properties of the tissues, the arrangement and features of the light emitters and the photodetector, or the influence of the measuring area, as well as motion artefacts and other sources of low-frequency noise; 3) isolating the influence of the arterial blood considering the pulsating component of the received signals. In the preferred embodiment, the measuring unit (2) comprises the following modules, referred to in FIG. 2:

a) a measuring module (4), which incorporates the components for the non-invasive measurement of glucose level;

b) a first computer module (5), responsible for activating some components of the measuring module (4) and a first part of the processing associated with the glucose level estimation starting from the data provided by the measuring module (4);

c) a first communications module (6), which is responsible for receiving configuration commands and sending data associated with the first computer module (5);

d) a first data storage module (7), for the temporary storage of the information in the event of communication failure, or for the persistent recording of the information from the measuring unit (2);

e) a pushbutton (8), for activating the measuring unit (2);

In turn, the measuring module (4) comprises the following components, referred to in FIG. 3:

a) A first light emitter E1 (9), activatable from the first computer module (5), with a wavelength corresponding to a maximum absorbance in the absorption spectrum of the glucose molecule within the near-infrared range, which strikes on the skin of a human area body (10) irrigated by a vascular bed. In one embodiment of the invention the wavelength corresponding to 950 nm is used, although other wavelengths are possible.

b) A second light emitter E2 (11), also activatable from the first computer module (5) and with a wavelength corresponding to a minimum absorbance in the absorption spectrum of the glucose molecule, located in a close manner to the first emitter E1 (9), and which affects the same area of the skin (10). In one embodiment of the invention the wavelength corresponding to 660 nm is used, although other wavelengths are possible.

c) A photodetector (12) sensitive to the wavelength of the first and second emitters (9, 11), which generates an electrical current signal S1 the amplitude of which depends on the intensity of light received in the sensitivity spectrum of the photodetector (12). In a preferred embodiment, the sensitivity spectrum of the photodetector integrates the wavelengths corresponding to 660 nm and 950 nm.

d) When the signal S1 is very weak, a first amplification step (13) generates the electrical voltage signal S2 amplified from signal S1.

e) A first filtering step (14) which abstracts the components of signal S2 which vary as a consequence of the arterial blood flow in the vascular bed, generating signal S3. In a preferred embodiment, this step is performed by means of a high-pass filter with a cut-off frequency which enables the pulsating components related to cardiac activity to pass.

f) When the signal S3 is very weak, a second amplification step (15) which generates the amplified signal S4 starting from the signal S3.

g) A second filtering step (16) which abstracts the components of signal S2 related to stationary properties in the measurement (light level emitted, stationary properties of the tissues, arrangement and features of the light emitters and the photodetector (12), or the influence of the measuring area (10)), which may vary from one measurement to another, as well as possible motion artefacts and other low-frequency error sources, generating signal S5. In a preferred embodiment, this step is performed by means of a low-pass filter with a cut-off frequency which does not enable the pulsating components related to cardiac activity to pass.

The information generated by the measuring unit (2) is transmitted wirelessly to the personal monitoring device (3), with which it maintains a bidirectional communications link. The start time of the measurement can be activated locally by means of a pushbutton (8) on the measuring unit (2) or it can be activated remotely by means of sending a command from the personal monitoring unit (3). Also by means of another command, the time instants wherein the automatic glucose estimations would be performed could be previously configured.

Figure 4:
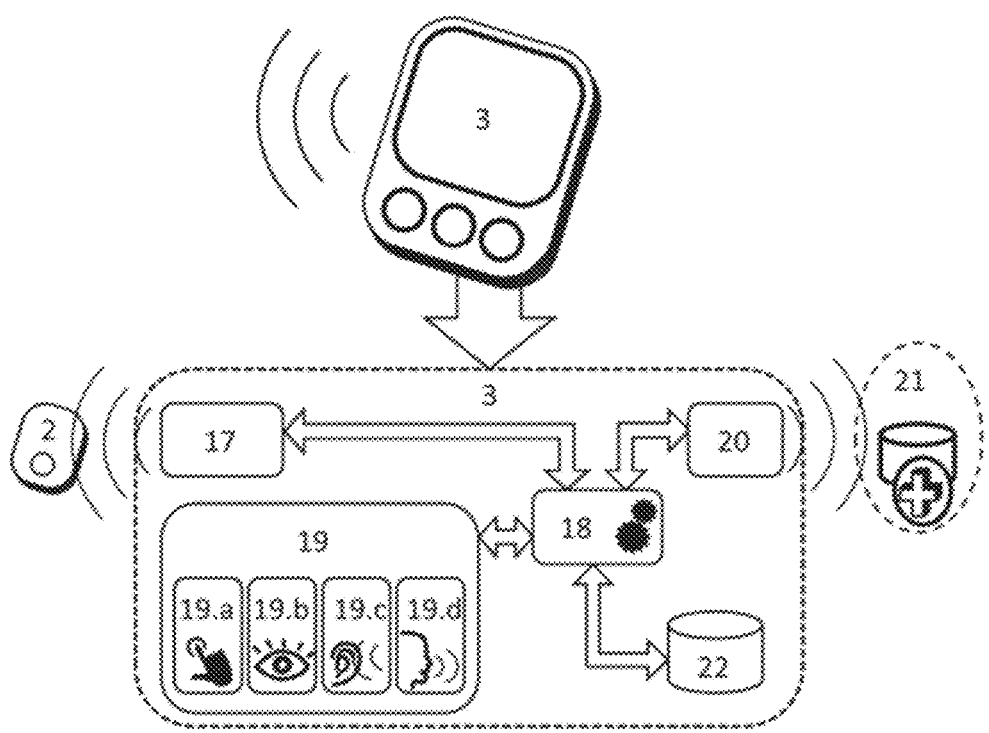
FIG. 4 shows a diagram of the basic architecture of the personal monitoring unit.

In the personal monitoring unit (3), with greater capabilities, both in terms of hardware and software, than the measuring unit (2), the part of processing with the greatest computational load associated with the method for glucose level estimation is developed. The multilevel distribution of the processing favours energy saving and reduces the computational load. The personal monitoring unit (3) can also be responsible for the processing and the management of the information coming from other portable sensors connected to it, which can be related to other physiological variables (respiratory rhythm, heart rate, ECG, heart rate variability, body temperature, physical activity, falls, body composition, skin impedance and pulse oximetry, etc.). In the preferred embodiment, the personal monitoring unit (3) comprises the following modules, referring to FIG. 4:

a) A second communications module (17) intended to establish bidirectional wireless communications with at least the measuring unit (2).

b) A second computer module (18) responsible for the second part of the processing associated with glucose level estimation. Algorithms for the detection of alarm situations or situations which should be considered worthy of attention are also executed in it.

c) An interface module (19) for displaying the information from the measuring unit (2) and the results from the second computer module (18), and enabling the user to interact in an adapted manner: touch (19.a), visual (19.b), auditory (19.c), or voice control (19.d), etc. If an alarm event is detected, the interface (19) includes adapted warning means (light, acoustic, vibrations, etc.). The user could then deactivate or silence the alarm while he manages and reviews the information provided. The interface (19) can be used by two types of users: the monitored user, which could occur in a home environment, or the professional user, which could occur in a clinical environment.

d) A third communications module (20) intended to establish bidirectional wireless communications with an external service provider (21).

e) A second data storage module (22) which is responsible for the temporary storage of the information from the personal monitoring unit (3) in case of communication failure, or for the persistent recording of such information, which enables the future access thereof without needing a remote connection to an external database.

In a preferred embodiment of the invention, the personal monitoring unit (3) is portable, although in other possible embodiments it can also be a fixed installation. Such device can be implemented physically by means of a smartphone or a tablet.

The measuring unit (2) and the personal monitoring unit (3) maintain a real-time timing system in order to manage the instants of measurement and the time periods of the operations. This timing system is also responsible for assigning to each estimation the instant in time in which they are performed. The personal monitoring unit (3) is responsible for coordinating the realization of the glucose estimations according to a pre-established plan, which can be configured by an expert user locally through the interface (19) of the device or remotely through telematic services of the e-Health system. Such estimations will be activated in the measuring unit (2) by means of sending a command. A hierarchical procedure is established from the personal monitoring unit (3) to the measuring unit (2) based on the sending of commands for the synchronisation of the timing systems. The different users, both experts and monitored users, can also activate the instantaneous performance of an estimation. This instantaneous activation can be performed from the pushbutton (8) of the measuring unit (2) or from the interface (19) of the personal monitoring unit (3).

The personal monitoring unit (3) can manage the information in an autonomous manner, including alarm management, establishing communications in a seamless manner to the user with the measuring unit (2) and with an external service provider (21) in order to integrate information and the alarms in an e-Health system.

Figure 5:
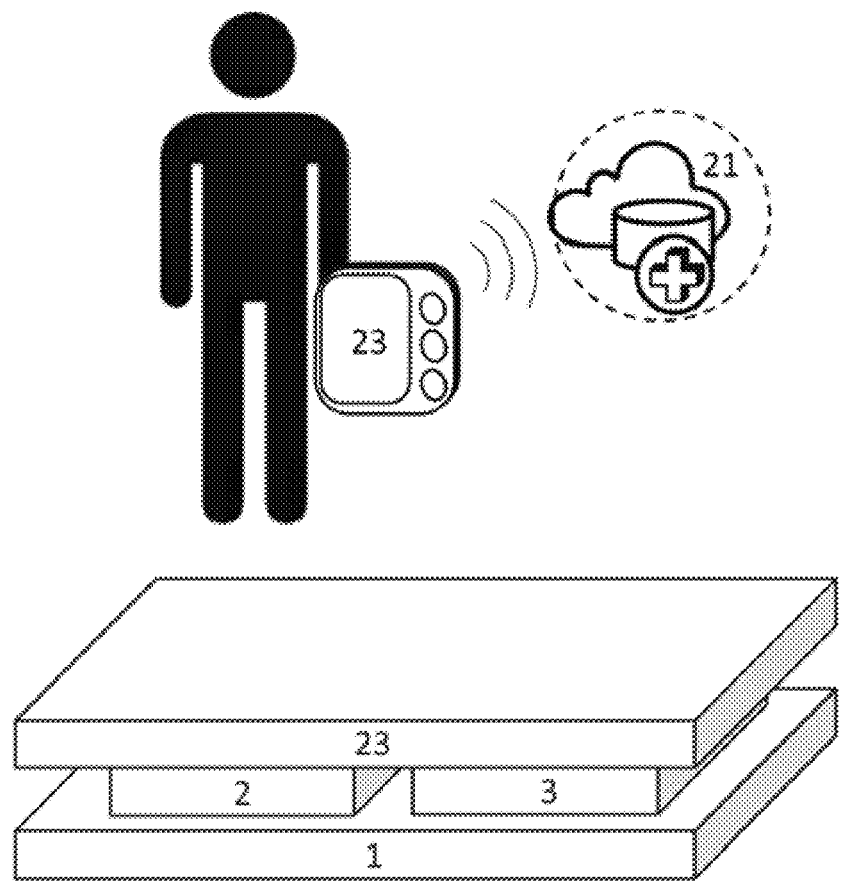
FIG. 5 shows a diagram of the monolithic device which combines the measuring unit and the personal monitoring unit.

The structural and functional modularity of the device for the non-invasive blood glucose level estimation enables two possible configurations: a distributed one (1), wherein the measuring unit (2) is physically separated from the personal monitoring unit (3), and another monolithic one, shown in FIG. 5, wherein the measuring unit (2) is integrated together with the personal monitoring unit (3) in a single device (23). In this second case, the communications between both units can be performed directly or wired (not wireless). Furthermore, the measuring unit (2) and the personal monitoring unit (3) can share physical components in the monolithic configuration (device (23)), such as a single computer module.

In a preferred embodiment of the invention, the first and second light emitters E1 and E2 (9, 11) are arranged such that the light beams cross through a relatively translucent body area (10) (a finger, for example), and are captured by a photodetector (12) located on the opposite side of the body area. This first embodiment is focused on the incorporation of the measuring unit (2) in a casing opaque to the spectrum of light wherein the photodetector (12) is sensitive, which is configured to maintain a constant pressure on the measuring area (10).

In another embodiment, and as FIG. 1 also shows, the measuring unit (2) incorporates a temperature module (24), which is responsible for measuring the temperature of the measuring area (10), such that the glucose estimation model incorporates this data in order to adjust the coefficients as a function of the temperature.

In addition to the components and elements making up the device object of the patent (1), it is also characterised in the method used for the non-invasive blood glucose level estimation, which is performed in a distributed manner in two levels: a first level of processing in the measuring unit (2), and a second level of processing in the personal monitoring unit (3). Thus, a distributed processing architecture and methodology are established, which is advantageous in terms of computing and energy saving. In terms of computing, because such multilevel structure enables the processing load between the two devices to be compensated for in order to prevent computational overload. In terms of the energy, because the highest energy consumption in portable devices is related to sending data wirelessly. As multilevel processing reduces and abstracts the wireless information to be transmitted, energy saving is thus favoured.

Figure 6:
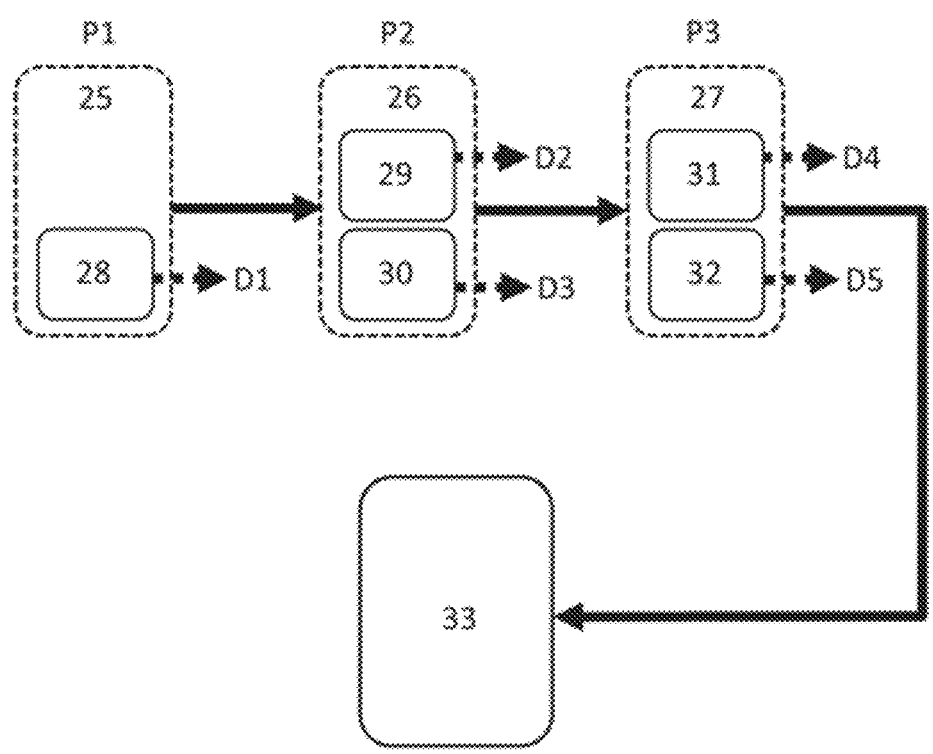
FIG. 6 illustrates the method for non-invasive blood glucose level estimation.

Said method comprises the following operations, referring to FIG. 6:

a) During a pre-configured time period P1 (25) wherein the first and second light emitters E1 and E2 (9, 11) are deactivated, the estimation (28) is performed of the parameter D1 as the average value of the signal S5.

b) During a second pre-configured time period P2 (26) wherein the first emitter E1 (9) is activated, and the second emitter E2 (11) is deactivated, the estimation (29) is performed of the parameter D2 as the average value of the signal S5.

c) During that same time period P2 (26), the estimation (30) is performed of the parameter D3 as the average value of the differences between successive maxima and minima identified in the pulsating signal S4 related to the cardiac activity.

d) During a third pre-configured time period P3 (27) wherein the second transmitter E2 (11) is activated, and the first transmitter E1 (9) is deactivated, the estimation (31) is performed of the parameter D4 as the average value of the signal S5.

e) During that same time period P3 (27), the estimation (32) is performed of the parameter D5 as the average value of the differences between successive maxima and minima identified in the pulsating signal S4 related to the cardiac activity.

f) Estimation (33) of the blood glucose level starting from a model which depends on the parameters D1, D2, D3, D4 and D5. The model isolates the influence of the glucose by weighting the dependence with respect to the parameters according to two conditions: with the glucose molecules subjected to a light associated with a maximum absorbance in the parameters D2 and D3, or subjected to a light associated with a minimum absorbance in the parameters D4 and D5. The influence of the ambient light on the measurement of the photodetector (12) is weighted in the dependence with respect to the parameter D1. The influence of the signal components related to stationary properties in the measurement (light level emitted, stationary properties of the tissues, arrangement and features of the light emitters and the photodetector (12), or the influence of the measuring area (10)), as well as possible motion artefacts and other error sources generated by low-frequency signals, is weighted in the dependence with respect to the parameters D2 and D4. The model isolates the influence of the arterial blood on the estimation, and eliminates the influence of other tissues, weighting the dependence with respect to the parameters D3 and D5.

The dependence of the model for glucose level estimation with respect to the parameters D1, D2, D3, D4 and D5 is based on coefficients which can be remotely configured by means of sending commands. The value of the coefficients is fixed by means of a quantitative method (least squares methods, genetic algorithms, swarm intelligence or neural networks), which minimises the mean square error of the estimations in a reference study, which is used as a calibration method. There are three possible models for glucose level estimation as a function of the coefficients: 1) a generalised model, wherein the value of the coefficients is adapted for the use of the model in multiple users; 2) a customised model, wherein the value of the coefficients is adjusted in order to optimise the glucose estimations for a given user; 3) a generalised and customisable model, which includes the dependence with other parameters related to the particular characteristics of the user, such as age, sex, the type of diabetes or the context of the measuring.

It is also possible to select the method of representing the glucose level estimation in the user interface (19): text, graphic, auditory, etc. or a multiple selection thereof. Furthermore, this proposal adds the possibility of selecting the classification method of the user, based on the results of the estimation. The selected classification method will establish thresholds based on the blood glucose level, which will enable the user to be classified into different levels, for example: very high, high, normal, low or very low. The thresholds, levels and the result of the classification will be displayed in a manner related to the representation method selected for the estimation (text, graphic, auditory, etc. or a multiple selection thereof). The classification method assumes prior clinical knowledge and classification standards in order to provide direct information about the state of the user and thus facilitate their evaluation and diagnosis.

The possibility of performing a historical tracking of the glucose estimations in the different measurements of a user is further considered. Such historical record will be displayed in a manner related to the selected representation method (text, graphic, auditory, etc. or a multiple selection thereof). In each of the measurements, the date and time when the estimation was performed can be identified.

The object of the invention may comprise additional processing on the record of the measurements which has the object of automatically establishing trends, patterns and predictions in the history of the measurements, which may be notified to the user.

The second computer module (18) also implements a system for detecting undesirable situations, which, if detected, would generate a series of local and remote alarms which would enable preventive action on the user. Such system uses a library of locally or remotely configurable indicators and a table with critical values for the generation of alarms related to said indicators. These indicators can be associated with a specific glucose estimation, but also with an analysis of trends, patterns and predictions of the history of the estimations. The logic and the decision rules which govern the activation of the alarms can also be configured to relate one or more of the indicators.

The invention claimed is:

1. A method for non-invasive blood glucose level estimation using a device comprising:
   a measuring arrangement, comprising a measuring module and a first computer module connected to the measuring module, wherein the measuring module comprises:
     a first light emitter directed to a relatively translucent body area;
     a second light emitter directed to a relatively translucent body area;
     one photodetector, located on an opposite side of the relatively translucent body area regarding the first light emitter and the second light emitter;
     a first signal amplifier, connected to the photodetector;
     a first high-pass filter, connected to the first signal amplifier;
     a second low-pass filter, connected to the first signal amplifier
     a second signal amplifier, connected to the first high-pass filter;
   a personal monitoring unit, physically separated from the measuring arrangement, and comprising a second computer module;
   the method comprising the steps of:
   emitting, by means of the first light emitter, an optical signal with a wavelength corresponding to a maximum absorbance in the absorption spectrum of the glucose molecule within the near-infrared range, which strikes on a skin surface of a body area irrigated by a vascular bed;
   emitting, by means of the second light emitter arranged close to the first light emitter, an optical signal with a wavelength corresponding to a minimum absorbance in the absorption spectrum of the glucose molecule;
   generating, by means of the photodetector, an electric current signal, the amplitude of which depends on the intensity of the light received in the sensitivity spectrum of the photodetector;
   generating, by means of the first signal amplifier, an electrical voltage signal, amplified from the electric current signal;
   generating a third signal by abstracting the components of the electrical voltage signal which vary due to the arterial flow, by means of the first high-pass filter with a cut-off frequency which enables the pulsating components related to the cardiac activity to pass;
   generating a fourth signal as an amplified signal from the third signal, by means of the second signal amplifier;
   generating a fifth signal by abstracting the components of the electrical voltage signal related to stationary properties in the measurement and low-frequency noise, by means of the second low-pass filter with a cut-off frequency which does not enable the pulsating components related to the cardiac activity to pass; and
   obtaining the blood glucose level in a distributed manner by using the first computer module and the second computer module, comprising the steps of:
   performing an estimation of a first parameter as an average value of the fifth signal during a first pre-configured time period wherein the first and second light emitters are deactivated;
   performing an estimation of a second parameter as the average value of the fifth signal during a second pre-configured time period wherein the first emitter is activated, and the second emitter is deactivated;
   performing an estimation of a third parameter during that second pre-configured time period, wherein the third parameter corresponds to an average value of differences between successive maxima and minima identified in the fourth signal;
   performing an estimation of a fourth parameter as an average value of the fifth signal during a third pre-configured time period wherein the second emitter is activated, and the first emitter is deactivated;
   performing an estimation of a fifth parameter during the third pre-configured time period, wherein such fifth parameter corresponds to an average value of differences between successive maxima and minima identified in the fourth signal;
   estimating the blood glucose level starting from a model which depends on the parameters from the first to the fifth wherein the model weights a dependence with respect to these parameters, thus isolating an influence of glucose according to two conditions: with glucose molecules subjected to a light associated with the maximum absorbance in the second parameter and third parameter or subjected to a light associated with the minimum absorbance in the fourth parameter and the fifth parameter and wherein an influence of ambient light in the measurement of the photodetector is weighted in the dependence with respect to the first parameter, and
   wherein an influence of signal components related to stationary properties in the measurement and low-frequency noise is weighted in the dependence with respect to the second and fourth parameters, and the model weights the dependence with respect to the third and fifth parameters, in order to isolate an influence of arterial blood in the estimation, and eliminate influence of other tissues.

2. The method of claim 1 wherein the dependence of the model for glucose level estimation with respect to the first to fifth parameters is performed based on coefficients which can be configured remotely by means of sending commands, and wherein values of the coefficients generate a generalised model for use in different users, or a customised model for an individual use, or a generalised and customisable model including a dependency with other parameters related to particular characteristics of the user.

3. The method of claim 1 further comprising activating an alarm locally and remotely when the glucose estimation records a value considered unsuitable.

4. The method according to claim 1, wherein the non-invasive blood glucose level estimation is performed in pre-configured time instants according to a pre-established plan.

* * * * *